United States Patent [19]

Edy

[11] 4,168,261
[45] Sep. 18, 1979

[54] METHOD FOR THE PURIFICATION OF INTERFERON USING POROUS GLASS BEADS

[75] Inventor: Victor G. Edy, Korbeek-LO, Belgium

[73] Assignee: Stichting Rega v.z.w., Louvain, Belgium

[21] Appl. No.: 794,079

[22] Filed: May 5, 1977

[30] Foreign Application Priority Data

May 28, 1976 [NL] Netherlands ............ 7605805

[51] Int. Cl.$^2$ ............................................. A61K 45/02
[52] U.S. Cl. ................................... 260/112 R; 424/85
[58] Field of Search ..................... 260/112 R, 112 B; 424/85

[56] References Cited

U.S. PATENT DOCUMENTS

| 3,144,390 | 8/1964 | Burke | 424/85 |
| 3,256,152 | 6/1966 | Lampson | 424/85 |
| 3,265,581 | 8/1966 | Fantes et al. | 424/85 |
| 3,414,651 | 12/1968 | Fantes | 424/85 |
| 3,560,611 | 2/1971 | Chany et al. | 424/85 |
| 3,699,222 | 10/1972 | Isaacs et al. | 424/85 |
| 3,975,344 | 8/1976 | Schwartz | 424/85 |
| 4,100,150 | 7/1978 | Cartwright | 260/112 R |

OTHER PUBLICATIONS

J. Gen. Virol. 33, pp. 517–521 (Dec. 1976), Edy et al.
Chem. Abstracts, vol. 86, 1977, 69861z, Edy et al.
Chem. Abstracts, vol. 68, 1968, 111438x, Fantes.
Science 1976, 191 (pp. 380–383), Bock et al.
Nature, vol. 206, 693–696 (1965), Haller.
Chem. Abstracts, vol. 78, 1973, 316, 122421u, Katsoyannis et al.

Primary Examiner—Howard E. Schain
Attorney, Agent, or Firm—Birch, Stewart, Kolasch and Birch

[57] ABSTRACT

An aqueous interferon solution which comprises contaminating proteins can be purified by chromatography on porous glass beads. The elution is effected at an acid pH.

7 Claims, No Drawings

METHOD FOR THE PURIFICATION OF INTERFERON USING POROUS GLASS BEADS

This invention relates to a method for the purification of interferon.

Interferon is the name given to an antiviral material which may be recovered from living cells and from extracellular fluids. Its production in the cells may be stimulated by various agents, most notably viruses, by ranging from bacteria to high molecular weight polymers. Interferon may be recovered from the cells or extracellular fluids in different degrees of purity, and appears to be capable of protecting animal tissues and cells against attack by viruses. In general, the antiviral activity is non-specific in the sense that treatment of animal tissues and cells protects against attack by a wide range of viruses, although viruses do differ in their sensitivity to interferon. In most cases, interferon is found to give better protection to tissues and cells of the kind from which it has been produced than to other tissues and cells.

General surveys of present knowledge about interferon may be found in the books "Interferon and Interferon Inducers", by N. B. Finter (ed.), North-Holland Publishing Co., Amsterdam, 1973 and "Selective Inhibitors of Viral Functions", by W. A. Carter (ed.), CRC-Press, Cleveland, 1973, which are incorporated herein by way of reference.

Complete or partial purification of interferon is necessary both for studies on the chemical character of interferons, and for its clinical application. Although many purification techniques have been described for the partial purification of interferons, all suffer from some deficiency. These deficiencies are generally either that only a low fraction of the total initial interferon activity is recovered in a purified form, or that specially prepared adsorbants are necessary. Therefore, there exists a need for a purification method of interferon which leads to a high recovery of activity, yet does not require complex reagents.

As a result of extensive research, it has now been found that a good purification of interferon without substantial losses of activity and without use of complex reagents, may be obtained by subjecting an aqueous interferon solution to chromatography on porous glass beads. If an interferon solution comprising contaminating proteins is contacted with the porous glass beads, the interferon will be selectively adsorbed onto these glass beads and the bulk of contaminating proteins will remain in solution and may be washed away. The adsorbed interferon may thereafter be eluted from the glass beads at acid pH. After elution, the glass beads may be reclaimed and the method may be repeated several times with the same glass beads since this adsorbent is extremely stable.

Thus, the invention provides a method for the purification of interferon, which is characterized by subjecting an aqueous interferon solution which comprises contaminating proteins as well, to chromatography on porous glass beads.

It should be noted here that porous glass beads have been proposed earlier for chromatographic purposes; compare an article by H. G. Bock et al in Science, Vol 191, 380–383 (1975). They were recommended there for utilization in the chromatography of several types of proteins and endotoxins. Any utilization of such glass beads for selectively adsorbing interferon from solution, however, has not been suggested up till now. Moreover, the aforesaid article describes the use of slightly alkaline buffer solutions for eluting proteins and other substances from the adsorbent and it contains no suggestion concerning the surprising fact that, contrary to all such proteins and substances, interferon can only be eluted from the glass beads at acid pH.

The starting material for effecting the purification method of the present invention may be any aqueous interferon solution which comprises contaminating proteins and which will need purification. Such solution may result from any stage in the production of interferon and may comprise any interferon type. Good results have been obtained with starting solutions containing human embryo fibroblast interferon and L-929 mouse interferon although other types of interferon may be equally suitable. Good results have further been obtained with a solution of interferon in Eagle's minimal essential medium (compare Science, 130, 432 (1959) or the book of John Paul, "Cell and Tissue Culture", Churchill Livingstone 1975, page 108) but other aqueous mediums should be equally possible and usable.

The porous glass beads to be used as an adsorbent are available on the market under several Trade Marks and are frequently indicated as having a "controlled pore size". They may conveniently be packed into a column for semi-continous operation but it will be understood that simple batch-type operations are equally well possible.

The starting solution is then contacted with the porous glass beads for selective adsorption of the interferon. Such contact may be effected by passing the starting solution over a column packed with the glass beads or by shaking it with an amount of such beads in a container. The contact leads to an adsorption of interferon from solution onto the glass beads whilst the bulk of contaminating proteins as present in solution will not be bound by the beads and will remain in solution.

The pH during contact will be the pH of the starting solution. This pH will normally be about 7.4 if Eagle's essential medium has been used although in general the system will work well for starting pHs between 7.0 and 9.2. Above pH 9.2, some activity is lost and much of the applied interferon is not adsorbed to the glass, but passes straight through the column.

The duration of the contact is not bound to critical limits although its value should of course be sufficient to have nearly all interferon adsorbed onto the beads; this duration may normally vary between 0.5 and 26 hours.

After contact, the remaining solution may be removed and the glass beads may be washed with a conventional washing agent such as a phosphate containing saline solution to remove any unbound contaminating proteins. Further washings may be effected with a special buffer solution such as a 0.01 M glycine-HCl buffer of pH 2.5 for removing any contaminating proteins that inadvertently have been bound to the column. The ionic strength of this glycine-HCl buffer is rather critical and should not go over 0.05 M since higher values (such as 0.1 M) would elute large amounts of interferon.

After the washing step, the interferon may be eluted from the glass beads with the aid of an acid aqueous solution. This solution may in general have a pH between 2 and 7. No good elution will be obtained at pH values above 7 and instability of the eluted interferon will be provoked at pH values below 2. Good results have been obtained with an elution agent comprising a 0.1. molar KCl-HCl buffer of pH 2.0. With the aid of such a buffer solution, substantially all of the adsorbed interferon may be eluted from the glass beads.

After elution, the glass beads may be washed and reclaimed, e.g. by rinsing them with strong acids for several days or heating them on a steam bath with 10% nitric acid followed by repeated rinsing with water to neutrality. Thereafter, they may be used again for chromatography of interferon in the abovedescribed way.

The result of the elution step is an aqueous interferon solution which still comprises substantially all of the interferon activity of the starting solution and which further comprises only a small content of contaminating proteins.

If the mutual ratio of interferon to contaminating proteins in the end product is compared with the same ratio in the starting material, then it appears that a high degree of purification has been reached. In practice, purification degrees of 40-fold to 90-fold have been obtained in a single operation. Should such value be deemed insufficient yet, then it can be improved by repeating the whole purification method but it will be understood that normally such repetition will not be necessary.

The following examples are meant for illustration purposes only, and not for limitation of the scope of the invention.

EXAMPLE 1

The starting material was a solution of human interferon derived from cells of the human embryo fibroblast type stimulated with the interferon inducer polyinosinic-polycytidylic acid. The interferon was in Eagle's minimal essential medium of pH 7.4, containing 1% by volume of Human plasma protein fraction, and had an activity of 25,000 interferon units per milliliter (determined by biological assay). The protein concentration of the interferon preparation was 0.45 milligrams per milliliter. Seventy-five milliliters of such interferon solution was applied to a column of Controlled Pore Glass beads (Electro-Nucleonics, Inc.), CPG-10 350, 0.9 cm × 11.8 cm. After washing the column with 35 ml phosphate buffered saline, a small amount, 56,000 units (3%), of the interferon was eluted by treatment with 33 ml of 0.01 M glycine-HCl buffer, pH 2.1. The bulk of the interferon was only eluted with 75 ml of 0.1 M potassium chloride-HCl. Of 1,875,000 units of interferon, containing a total of 34 mg of contaminating protein, 1,080,000 units were recovered by elution (58% of the original total), and containing a total of 0.22 mg of contaminating proteins. This represents a purification of 90-fold.

It follows from the data presented in this example that a considerable degree of purification of human fibroblast interferon can be achieved by chromatography on porous glass beads, under conditions where the great bulk of the contaminating proteins does not bind.

EXAMPLE 2

The starting material was a solution of mouse interferon derived from cells of the L-929 type, stimulated by Newcastle Disease virus. The interferon was in Eagle's minimal essential medium of pH 7.4 and had an activity of 16,000 interferon units per milliliter (determined by biological assay). The protein concentration of the interferon preparation was 0.64 milligrams of contaminating proteins per milliliter. 200 ml of such interferon solution was applied to a column of CPG-10 350, 0.9 × 12.5 cm. After washing the column with 64 ml of phosphate buffered saline, and 70 ml of 0.01 M glycine-HCl buffer, pH 2.1, interferon was eluted with 128 ml of 0.1 M potassium chloride-HCl. Of 3,200,000 units of interferon, containing a total of 100 milligrams of contaminating proteins, 1,990,000 units were recovered by elution (62% of the original total), containing a total of 1.95 mg of contaminating protein. This represents a purification of 41-fold.

It follows from this Example that purification of mouse interferon, as well as human interferon, may be achieved by chromatography on porous glass beads.

What I claim is:

1. A method for the purification of an aqueous interferon solution containing contaminating proteins which comprises subjecting said solution to chromatography on porous glass beads, and eluting the interferon from said beads at an acidic pH.

2. The method of claim 1, wherein the interferon is eluted from the glass beads with an aqueous solution having an acidic pH of at least 2.

3. The method of claim 2, wherein the elution is effected with a 0.1 M KCl-HCl buffer solution having a pH of 2.0.

4. The method of claim 1, wherein the glass beads are washed with a 0.01 M glycine-HCl buffer solution after adsorption of the interferon but before said elution step.

5. The method of claim 1, wherein the starting interferon solution comprises human fibroblast interferon.

6. The method of claim 1, wherein the starting interferon solution comprises mouse interferon.

7. The method of claim 1, wherein the pH of the starting interferon solution is between 7.0 and 9.2.

* * * * *

UNITED STATES PATENT AND TRADEMARK OFFICE
CERTIFICATE OF CORRECTION

PATENT NO. : 4,168,261
DATED : September 18, 1979
INVENTOR(S) : Victor G. EDY

It is certified that error appears in the above-identified patent and that said Letters Patent are hereby corrected as shown below:

IN THE HEADING:

Under [73] Assignee:

Change "Louvain" to read --Leuven--.

Signed and Sealed this

Eighth Day of January 1980

[SEAL]

Attest:

SIDNEY A. DIAMOND

Attesting Officer

Commissioner of Patents and Trademarks